(12) United States Patent
Liu et al.

(10) Patent No.: US 9,468,897 B2
(45) Date of Patent: Oct. 18, 2016

(54) PROCESS AND APPARATUS FOR IMPROVING LIGHT OLEFIN YIELD FROM A FLUID CATALYTIC CRACKING PROCESS

(71) Applicant: UOP LLC, Des Plaines, IL (US)

(72) Inventors: Kirk Liu, Chicago, IL (US); Zhihao Fei, Naperville, IL (US); Charles P. Luebke, Mount Prospect, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 14/578,181

(22) Filed: Dec. 19, 2014

(65) Prior Publication Data

US 2016/0175798 A1    Jun. 23, 2016

(51) Int. Cl.
| | |
|---|---|
| *B01J 8/26* | (2006.01) |
| *B01J 8/24* | (2006.01) |
| *C07C 4/06* | (2006.01) |
| *C10G 51/02* | (2006.01) |
| *C10G 51/06* | (2006.01) |

(52) U.S. Cl.
CPC .. *B01J 8/26* (2013.01); *B01J 8/24* (2013.01); *C07C 4/06* (2013.01); *C10G 51/026* (2013.01); *C10G 51/06* (2013.01); *B01J 2208/00893* (2013.01); *C07C 2529/06* (2013.01)

(58) Field of Classification Search
CPC ........ B01J 8/26; C10G 51/026; C10G 51/06; C10G 51/00; C10G 21/20; C10G 21/27; C10G 21/28
See application file for complete search history.

(56) References Cited

U.S. PATENT DOCUMENTS

| | | | |
|---|---|---|---|
| 6,538,169 B1 | 3/2003 | Pittman et al. | |
| 7,247,233 B1 | 7/2007 | Hedrick et al. | |
| 7,312,370 B2 | 12/2007 | Pittman et al. | |
| 2003/0220530 A1* | 11/2003 | Boelt | C07C 4/06 585/648 |
| 2011/0110825 A1* | 5/2011 | Leonard | C10G 11/00 422/187 |

OTHER PUBLICATIONS

U.S. Appl. No. 14/578,167, filed Dec. 19, 2014.

* cited by examiner

*Primary Examiner* — Lessanework Seifu

(57) ABSTRACT

The present invention discloses a process optimizing the yield of ethylene and propylene from a fluid catalytic cracking unit. The method combines a first catalytic reactor, a fractionation zone, a separation unit and a second catalytic reactor. The separation unit produces a first separate stream comprising $C_4$ olefins and a second separate stream comprising $C_5$ olefins. The separate streams may be combined and are passed to a second catalytic reactor for additional conversion to ethylene and propylene.

15 Claims, 5 Drawing Sheets

PROCESS AND APPARATUS FOR IMPROVING LIGHT OLEFIN YIELD FROM A FLUID CATALYTIC CRACKING PROCESS

BACKGROUND OF THE INVENTION

The disclosure relates to a separation process for improving ethylene and propylene yield.

Fluid catalytic cracking (FCC) is a catalytic hydrocarbon conversion process accomplished by contacting heavier hydrocarbons in a fluidized reaction zone with a catalytic particulate material. The reaction in catalytic cracking, as opposed to hydrocracking, is carried out in the absence of substantial added hydrogen or the consumption of hydrogen. Various products may be produced from such a process, including a naphtha product and/or a light product such as propylene and/or ethylene.

There have been several development efforts to increase the ethylene and propylene yield from an FCC unit. One of the solutions has been to recycle $C_4$ and $C_5$ olefin product back to the FCC unit in order to selectively crack these components to ethylene and propylene. Another solution is to recycle the olefins back to a second reactor optimized to convert the olefins to ethylene and propylene. In this case, a separate recovery section is needed to process the product from the second reactor. This configuration works well at low to moderate ethylene and propylene yields, but if higher yields are required, then the amount of material that needs to be recycled increases rapidly as the $C_4$ and/or $C_5$ paraffins are not separated from the $C_4$ and/or $C_5$ olefins in most FCC processes. As the paraffins cannot be rejected, this inert material must also be recycled in order to be able to recycle a greater amount of the olefin material.

Therefore, what is needed is a new process configuration which allows for the advantages of a traditional FCC unit configuration, but improves the overall configuration by allowing for the $C_4$ and/or $C_5$ paraffins to be separated from the $C_4$ and/or $C_5$ olefins. The overall FCC process recovery section is simplified compared to a process using the aforementioned second reactor as a common recovery section can be used.

SUMMARY OF THE INVENTION

An embodiment of the invention is a process for catalytic cracking comprising feeding a hydrocarbon feed stream to a first catalytic reactor. An effluent stream of the first catalytic reactor is passed to a fractionation section to produce a first fractionation stream comprising $C_4$ hydrocarbons. The first fractionation stream is passed to a separation unit to produce a first separated stream having a greater concentration of $C_4$ olefins than the first fractionation stream. The first separated stream is then fed to a second catalytic reactor.

Another embodiment of the invention is an apparatus for catalytic cracking comprising a first catalytic reactor for catalytically cracking a first hydrocarbon feed stream. A fractionation zone is in downstream communication with the first catalytic reactor. The fractionation zone comprises a debutanizer column. A separation unit includes a first distillation column in downstream communication with the debutanizer column for producing a first separated stream comprising $C_4$ olefins. A second catalytic reactor is in downstream communication with the separation unit for cracking a second hydrocarbon feed stream comprising the first separated stream.

These and other features, aspects, and advantages of the present invention will become better understood upon consideration of the following detailed description, drawings and appended claims.

BRIEF DESCRIPTION OF THE DRAWINGS

Like reference numerals will be used to refer to like parts from Figure to Figure in the following description of the drawings.

DETAILED DESCRIPTION OF THE INVENTION

As used herein, the following terms have the corresponding definitions.

The term "communication" means that material flow is operatively permitted between enumerated components.

The term "downstream communication" means that at least a portion of material flowing to the subject in downstream communication may operatively flow from the object with which it communicates.

The term "upstream communication" means that at least a portion of the material flowing from the subject in upstream communication may operatively flow to the object with which it communicates.

The term "direct communication" means that flow from the upstream component enters the downstream component without undergoing a compositional change due to physical fractionation or chemical conversion.

The term "column" means a distillation column or columns for separating one or more components of different volatilities which may have a reboiler on its bottom and a condenser on its overhead. Unless otherwise indicated, each column includes a condenser on an overhead of the column to condense and reflux a portion of an overhead stream back to the top of the column and a reboiler at a bottom of the column to vaporize and send a portion of a bottoms stream back to the bottom of the column. Feeds to the columns may be preheated. The top pressure is the pressure of the overhead vapor at the outlet of the column. The bottom temperature is the liquid bottom outlet temperature.

As used herein, the term "separator" means a vessel which has an inlet and at least two outlets for separating material entering the inlet to provide streams exiting the outlets.

The term "$C_x$ hydrocarbons" wherein "x" is an integer means hydrocarbons having x carbon atoms.

The term "$C_x^-$" wherein "x" is an integer means a hydrocarbon stream with hydrocarbons having x and/or less carbon atoms and preferably x and less carbon atoms.

The term "$C_x^+$" wherein "x" is an integer means a hydrocarbon stream with hydrocarbons having x and/or more carbon atoms and preferably x and more carbon atoms.

The term "predominant" means a majority, suitably at least 80 wt % and preferably at least 90 wt %.

DESCRIPTION OF THE INVENTION

Figure 1:
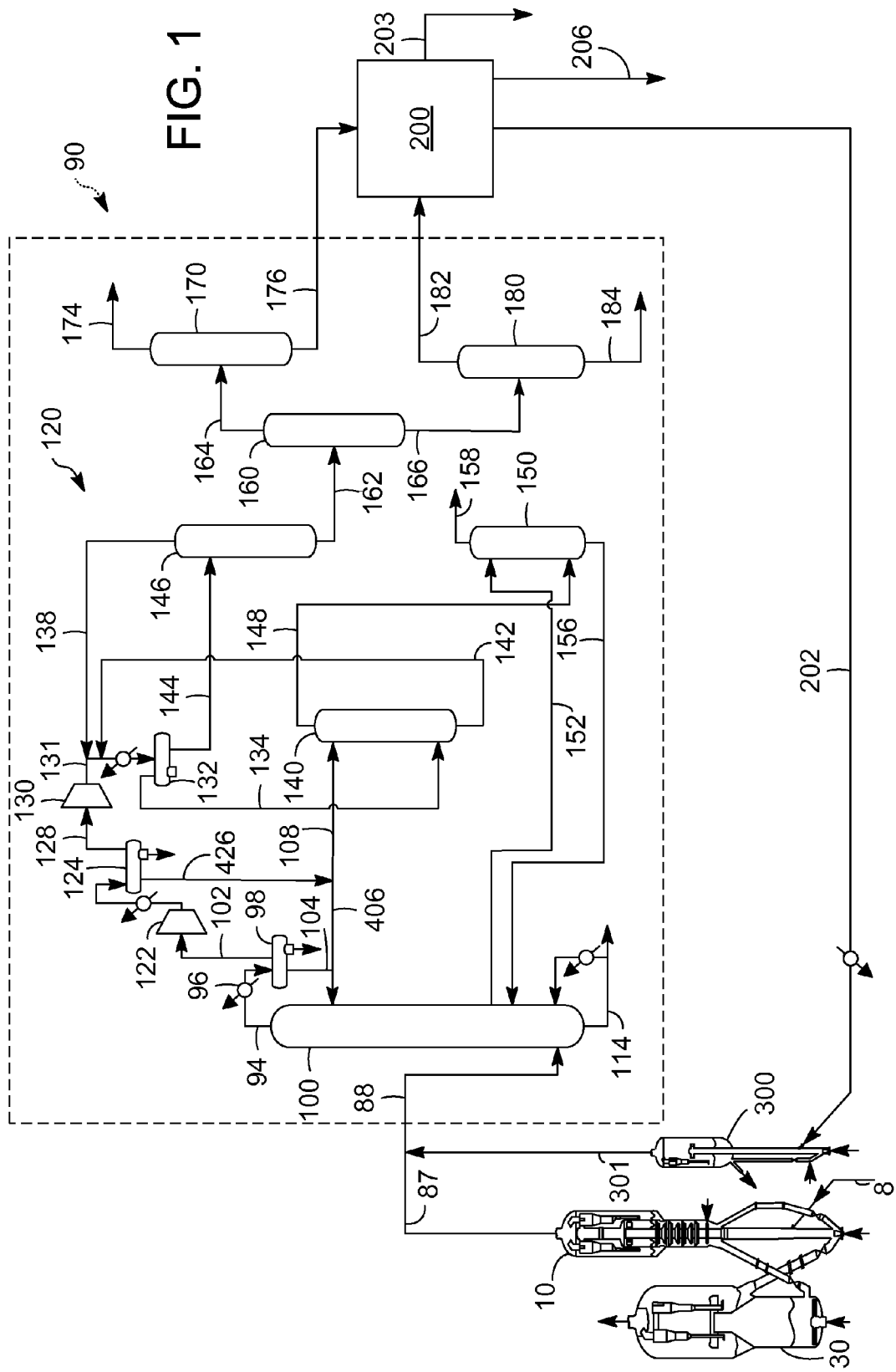
FIG. 1 is a process flow scheme for the present invention.
Figure 2:
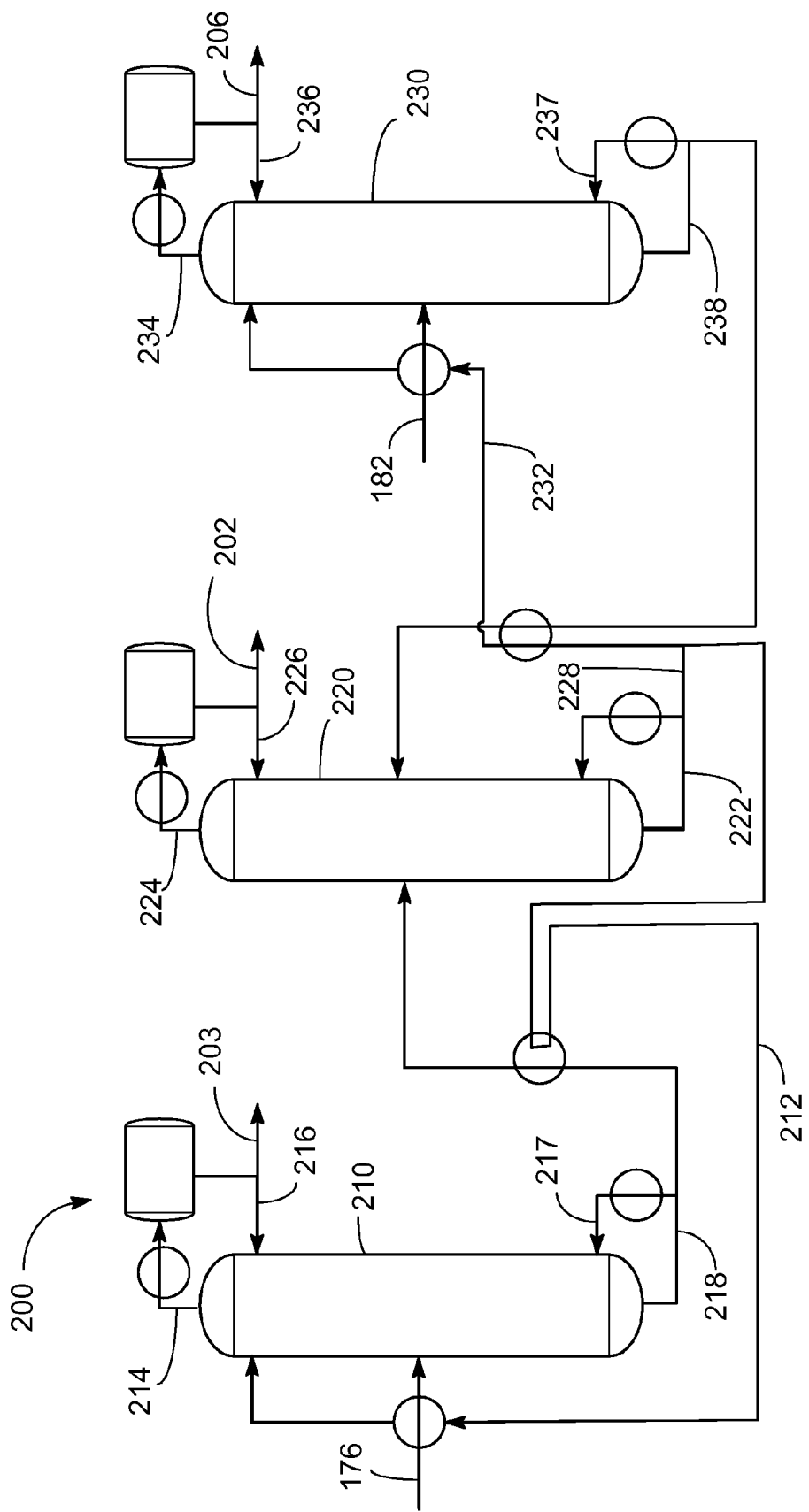
FIG. 2 is a process flow scheme for a separation unit used in the process of FIG. 1.
Figure 3:
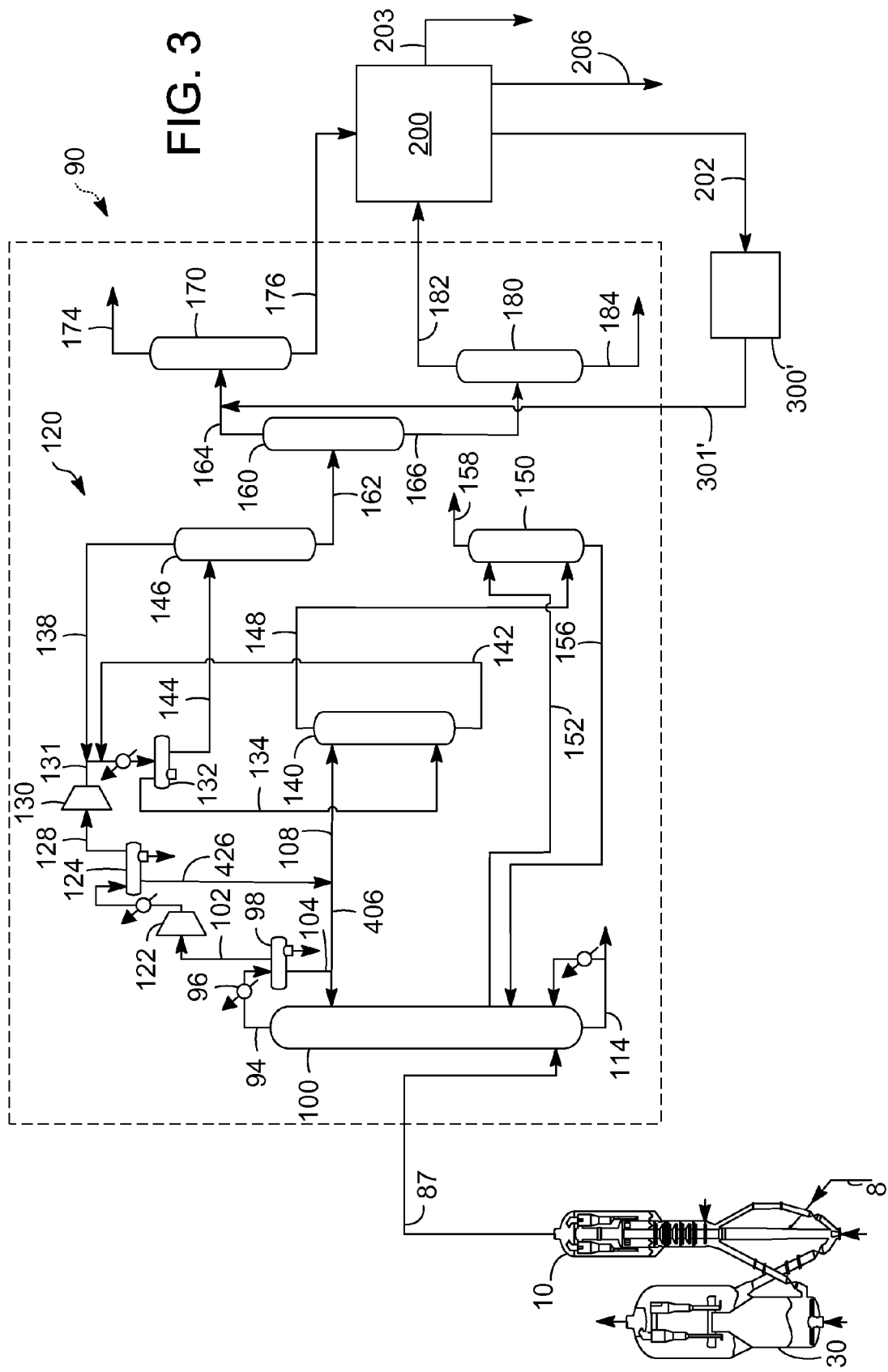
FIG. 3 is a process flow scheme for another embodiment of the present invention.

A general understanding of the process and apparatus of this invention can be obtained by reference to FIGS. 1-3.

FIGS. 1-3 have been simplified by the deletion of a large number of apparatuses customarily employed in a process of this nature, such as vessel internals, temperature and pressure controls systems, flow control valves, recycle pumps, etc. which are not specifically required to illustrate the performance of the invention. Furthermore, the illustration of the process of this invention in the embodiment of a specific drawing is not intended to limit the invention to specific embodiments set out herein.

Commercially there is a demand for FCC technology capable of producing high ethylene and propylene yields from conventional feedstocks. We have found that ethylene and propylene yield can be increased to a great extent economically by directing the $C_4$ and $C_5$ materials recovered from the fractionation zone to a separation unit. By selectively recovering the $C_4$ and $C_5$ olefins from the $C_4$ and $C_5$ paraffins and then passing the olefins to a second catalytic reactor, it is possible to increase the ethylene and propylene yield but with surprisingly significantly less capital and utility costs over that provided by an equivalent FCC process without a $C_4$ and $C_5$ materials separation unit.

One embodiment of the present invention is an apparatus and process that may be described with reference to four components shown in FIG. 1: a first catalytic reactor 10, a fractionation section 90, a separation unit 200, and a second catalytic reactor 300. Many configurations of the present invention are possible, but specific embodiments are presented herein by way of example. All other possible embodiments for carrying out the present invention are considered within the scope of the present invention.

The first catalytic reactor 10 may be an FCC reactor. A conventional FCC feedstock and higher boiling hydrocarbon feedstock are a suitable first hydrocarbon feed 8 stream to the first FCC reactor. The most common of such conventional feedstocks is a "vacuum gas oil" (VGO), which is typically a hydrocarbon material having a boiling range of from 343° to 552° C. (650° to 1025° F.) prepared by vacuum fractionation of atmospheric residue. Such a fraction is generally low in coke precursors and heavy metal contamination which can serve to contaminate catalyst. Heavy hydrocarbon feedstocks to which this invention may be applied include heavy bottoms from crude oil, heavy bitumen crude oil, shale oil, tar sand extract, deasphalted residue, products from coal liquefaction, atmospheric and vacuum reduced crudes. Heavy feedstocks for this invention also include mixtures of the above hydrocarbons and the foregoing list is not comprehensive. Moreover, additional amounts of feed may also be introduced downstream of the initial feed point.

The first catalytic reactor 10, which may be an FCC reactor, can operate at any suitable temperature, and typically operates at a temperature of about 150° to about 580° C., preferably about 520° to about 580° C. at the reactor outlet. In one exemplary embodiment, a high temperature may be desired, such as no less than about 565° C. at the outlet and a pressure of from about 69 to about 517 kPa (gauge) (10 to 75 psig) but typically less than about 275 kPa (gauge) (40 psig). The catalyst-to-oil ratio, based on the weight of catalyst and feed hydrocarbons entering the bottom of the reactor, may range up to 30:1 but is typically between about 4:1 and about 25:1. Hydrogen is not normally added to the reactor. Steam may be passed into the first reactor 10 equivalent to about 2 to 35 wt % of feed. Typically, however, the steam rate may be between about 2 and about 7 wt % for maximum gasoline production and about 10 to about 30 wt % for maximum light olefin production. The average residence time of catalyst in the reactor may be less than about 5 seconds.

The catalyst in the first catalytic reactor 10 can be a single catalyst or a mixture of different catalysts. Usually, the catalyst includes two components or catalysts, namely a first component or catalyst, and a second component or catalyst. Such a catalyst mixture is disclosed in, e.g., U.S. Pat. No. 7,312,370. Generally, the first component may include any of the well-known catalysts that are used in the art of FCC, such as an active amorphous clay-type catalyst and/or a high activity, crystalline molecular sieve. Zeolites may be used as molecular sieves in FCC processes. Preferably, the first component includes a large pore zeolite, such as a Y-type zeolite, an active alumina material, a binder material, including either silica or alumina, and an inert filler such as kaolin.

Typically, the zeolitic molecular sieves appropriate for the first component have a large average pore size. Usually, molecular sieves with a large pore size have pores with openings of greater than about 0.7 nanometers in effective diameter defined by greater than about 10, and typically about 12, member rings. Pore Size Indices of large pores can be above about 31. Suitable large pore zeolite components may include synthetic zeolites such as X and Y zeolites, mordenite and faujasite. A portion of the first component, such as the zeolite, can have any suitable amount of a rare earth metal or rare earth metal oxide.

The second component may include a medium or smaller pore zeolite catalyst, such as a MFI zeolite, as exemplified by at least one of ZSM-5, ZSM-11, ZSM-12, ZSM-23, ZSM-35, ZSM-38, ZSM-48, and other similar materials. Other suitable medium or smaller pore zeolites include ferrierite, and erionite. Preferably, the second component has the medium or smaller pore zeolite dispersed on a matrix including a binder material such as silica or alumina and an inert filler material such as kaolin. The second component may also include some other active material such as Beta zeolite. These compositions may have a crystalline zeolite content of about 10 wt % to about 50 wt % or more, and a matrix material content of about 50 wt % to about 90 wt %. Components containing about 40 wt % crystalline zeolite material are preferred, and those with greater crystalline zeolite content may be used. Generally, medium and smaller pore zeolites are characterized by having an effective pore opening diameter of less than or equal to about 0.7 nanometers, rings of about 10 or fewer members, and a Pore Index of less than about 31. Preferably, the second catalyst component is an MFI zeolite having a silicon-to-aluminum ratio greater than about 15, preferably greater than about 75. In one exemplary embodiment, the silicon-to-aluminum ratio can be about 15:1 to about 35:1.

The total catalyst mixture in the first reactor 10 may contain about 1 to about 25 wt % of the second component, including a medium to small pore crystalline zeolite with greater than or equal to about 7 wt % of the second component being preferred. When the second component contains about 40 wt % crystalline zeolite with the balance being a binder material, an inert filler, such as kaolin, and optionally an active alumina component, the catalyst mixture may contain about 0.4 to about 10 wt % of the medium to small pore crystalline zeolite with a preferred content of at least about 2.8 wt %. The first component may comprise the balance of the catalyst composition. In some preferred embodiments, the relative proportions of the first and second components in the mixture may not substantially vary throughout the first reactor 10. The high concentration of the medium or smaller pore zeolite as the second component of the catalyst mixture can improve selectivity to light olefins.

In one exemplary embodiment, the second component can be a ZSM-5 zeolite and the catalyst mixture can include about 0.4 to about 10 wt % ZSM-5 zeolite excluding any other components, such as binder and/or filler. Coke is deposited on the catalyst when it contacts the feed in the reactor 10. Coked catalyst is regenerated by combustion in the regenerator 30 and recycled back to the reactor 10.

A first effluent stream of the first catalytic reactor comprising first cracked products in the line 87 from the first catalytic reactor 10, relatively free of catalyst particles, exit the first catalytic reactor 10. The first effluent stream in the line 87 may be subjected to additional treatment to remove fine catalyst particles or to further prepare the stream prior to fractionation. The first effluent stream in the line 87 can be combined with a second effluent stream of a second catalytic reactor 300 comprising a second cracked products stream in a line 301 to produce a products stream in line 88. The line 88 transfers the cracked products streams to the fractionation section 90 that in an embodiment may include a main fractionation column 100 and a gas recovery section 120. The fractionation section fractionates the first effluent stream and into several streams which all may be generally referred to as a first effluent stream. It is contemplated that the second effluent stream be fractionated separately from the first effluent stream. The fractionation section 90 may separately fractionate the second effluent stream into several streams which all may be generally referred to as a second effluent stream.

The main column 100 is a fractionation column with trays and/or packing positioned along its height for vapor and liquid to contact and reach equilibrium proportions at tray conditions and a series of pump-arounds to cool the contents of the main column. The main fractionation column is in downstream communication with the first reactor 10 and second reactor 300 and can be operated with an top pressure of about 35 to about 172 kPa (gauge) (5 to 25 psig) and a bottom temperature of about 343° to about 399° C. (650° to 750° F.). In the product recovery section 90, the gaseous FCC product in line 88 is directed to a lower section of an FCC main fractionation column 100. A variety of products are withdrawn from the main column 100. In this case, the main column 100 recovers an overhead stream of light products comprising unstabilized naphtha and lighter gases in an overhead line 94. The overhead stream in overhead line 94 is condensed in a condenser and perhaps cooled in a cooler both represented by 96 before it enters a receiver 98 in downstream communication with the first reactor 10. A net overhead line 102 withdraws a light off-gas stream of liquefied petroleum gas (LPG) and dry gas from the receiver 98. An aqueous stream is removed from a boot in the receiver 98. A bottoms liquid stream of light unstabilized naphtha leaves the receiver 98 via a line 104. A first portion of the bottoms liquid stream is directed back to an upper portion of the main column and a second portion in line 406 may be directed to the gas recovery section 120. Both lines 102 and 406 may be fed to the gas recovery section 120. Several other fractions may be separated and taken from the main column including a light cycle oil stream in line 152 and an optional heavy slurry oil from the bottom in line 114.

The gas recovery section 120 is shown to be an absorption based system, but any vapor recovery system may be used including a cold box system. To obtain sufficient separation of light gas components, the gaseous stream in the net overhead line 102 is compressed in a compressor 122, also known as a wet gas compressor, which is in downstream communication with the main fractionation column overhead receiver 98. Any number of compressor stages may be used, but typically dual stage compression is utilized. In dual stage compression, compressed fluid from compressor 122 is cooled and enters an interstage compressor receiver 124 in downstream communication with the compressor 122. Liquid in line 426 from a bottom of the compressor receiver 124 and the unstabilized naphtha in line 406 from the main fractionation column overhead receiver 98 flow into a primary absorber column 140 in downstream communication with the compressor receiver 124 to serve as an absorbent. In an embodiment, these streams may join and flow into the primary absorbent column 140 together in line 108. In an embodiment not shown in FIG. 1, line 426 may flow into the primary absorber column 140 at a higher elevation than line 406 if the two streams are delivered separately. In an embodiment, the primary absorber column 140 is in direct downstream communication with the bottom of the overhead receiver 98 of the main fractionation column 100 and/or a bottom of the interstage compressor receiver 124. Gas in line 128 from a top of the compressor receiver 124 enters an optional second compressor 130, also known as a wet gas compressor, in downstream communication with the compressor receiver 124. The first compression stage compress gaseous fluids to a pressure of about 345 to about 1034 kPa (gauge) (50 to 150 psig) and preferably about 482 to about 690 kPa (gauge) (70 to 100 psig). The second compression stage compresses gaseous fluids to a pressure of about 1241 to about 2068 kPa (gauge) (180 to 300 psig).

Compressed effluent from the second compressor 130 in line 131 is joined by streams in lines 138 and 142, and gaseous components are partially condensed and all flow to a second compressor receiver 132 in downstream communication with the second compressor 130. Compressed gas from a top of the second compressor receiver 132 travels in line 134 to enter a primary absorber column 140 at a lower point than an entry point for the liquid stream in line 426 from a bottom of the compressor receiver 124 and the unstabilized naphtha in line 406 from the main fractionation column overhead receiver 98 via line 108. The primary absorber column 140 is in downstream communication with an overhead of the second compressor receiver 132. A liquid stream from a bottom of the second compressor receiver 132 travels in line 144 to a stripper column 146.

The gaseous hydrocarbon stream in lines 134 fed to the primary absorber column 140 is contacted with liquid stream in line 426 from a bottom of the compressor receiver 124 and the unstabilized naphtha in line 406 from the main fractionation column overhead receiver 98 via line 108 to effect a separation between $C_3^+$ and $C_2^-$ hydrocarbons by absorption of the heavier hydrocarbons into the naphtha stream upon counter-current contact. The primary absorber column 140 may utilize no condenser or reboiler but may have one or more pump-arounds to cool the materials in the column. The primary absorber column may be operated at a top pressure of about 1034 to about 2068 kPa (gauge) (150 to 300 psig) and a bottom temperature of about 27 to about 66° C. (80 to 150° F.). A liquid $C_3^-$ stream in line 142 from the bottoms of the primary absorber column is returned to line 131 upstream of condenser to be cooled and returned to the second compressor receiver 132. An off-gas stream in line 148 from a top of the primary absorber 140 is directed to a lower end of a secondary or sponge absorber 150. A circulating stream of light cycle oil (LCO) in line 152 absorbs most of the remaining $C_5^+$ material and some $C_3$-$C_4$ material in the off-gas stream in line 148 by counter-current contact. LCO from a bottom of the secondary absorber in line 156 richer in $C_3^-$ material than the circulating stream in line 152 is returned in line 156 to the main column 100. The secondary absorber column 150 may be operated at a top pressure just below the pressure of the primary absorber column 140 of about 965 to about 2000 kPa (gauge) (140 to 290 psig) and a bottom temperature of about 38 to about 66° C. (100 to 150° F.). The overhead stream of the secondary absorber column 150 comprising dry gas of predominantly $C_2^-$ hydrocarbons with hydrogen sulfide, amines and hydrogen is removed in line 158 and may be subjected to further separation to recover ethylene and hydrogen.

Liquid from a bottom of the second compressor receiver 132 in line 144 is sent to the stripper column 146. Most of the $C_2^-$ material is stripped from the $C_3$-$C_7$ material and removed in an overhead of the stripper column 146. The overhead gas in line 138 from the stripper column 146 comprising $C_2^-$ material, LPG and some naphtha is returned to line 131 without first undergoing condensation. The condenser on line 131 will partially condense the overhead stream from line 138 with the gas compressor discharge in line 131. The partially condensed overhead stream from line 138 and gas compressor discharge in line 131 will undergo vapor-liquid separation with the bottoms stream 142 from the primary absorber column 140 in the second compressor receiver 132. The stripper column 146 is in downstream communication with the first catalytic reactor 10, a bottom of the second compressor receiver 132 and a bottom of the primary absorber 140. The bottoms product of the stripper column 146 in line 162 is rich in naphtha. The stripper column may be run at a pressure above the compressor 130 discharge at about 1379 to about 2206 kPa (gauge) (200 to 320 psig) and a temperature of about 38 to about 149° C. (100 to 300° F.).

FIG. 1 shows that the liquid bottoms stream from the stripper column 146 comprising a first effluent stream may be passed to a debutanizer column 160 via line 162. The debutanizer column 160 is in downstream communication with the first catalytic reactor 10, a bottom of the second compressor receiver 132 and the bottom of the primary absorber 140. The debutanizer column 160 may fractionate a first effluent stream comprising a portion of first cracked products from the first catalytic reactor 10 to produce a $C_4^-$ overhead stream comprising a first fractionation stream and a $C_5^+$ bottoms stream. The first fractionation stream in overhead line 164 from the debutanizer column comprises $C_3$-$C_4$ olefinic product which can be passed to an LPG splitter column 170 which is in downstream communication with an overhead of the debutanizer column 160 to further refine the first fractionation stream. The debutanizer column may be operated at a top pressure of about 1034 to about 2068 kPa (gauge) (150 to 300 psig) and a bottom temperature of about 149 to about 204° C. (300 to 400° F.).

In the LPG splitter column 170, $C_3$ materials may be separated from the first fractionation stream and forwarded in an overhead stream in an overhead line 174. The overhead stream may be passed to a depropanizer column (not shown) to separate $C_3$ materials from lighter materials to further recover propylene and ethylene products. $C_4$ materials remaining in the first fractionation stream provided from the bottom of the LPG splitter column in line 176 is produced as the preferred first fractionation stream.

The separation unit 200 is in downstream communication with the LPG splitter bottoms line 176. In the separation unit 200, $C_4$ materials comprising olefins and paraffins are separated with $C_4$ olefins recovered from the separation unit in the line 202 and $C_4$ paraffins recovered in the line 203. The $C_4$ paraffin stream can be forwarded to be LPG product or further processed. The LPG splitter 170 may be operated with a top pressure of about 69 to about 207 kPa (gauge) (10 to 30 psig) and a bottom temperature of about 38 to about 121° C. (100 to 250° F.).

The debutanizer bottoms stream comprising $C_5$+ naphtha in the debutanizer bottoms line 166 comprising a first effluent stream may be passed to a depentanizer column 180 in downstream communication with said debutanizer column 160. In the depentanizer column $C_6$+ material is separated from $C_5$ material in the first effluent stream of the first catalytic reactor to produce a second fractionation stream comprising $C_5$ material from an overhead line 182 of the depentanizer column 180. A gasoline product stream in a depentanizer bottoms line 184 comprising $C_6$+ hydrocarbons from the depentanizer column bottom may be forwarded to the gasoline product pool or be further processed. The separation unit 200 is in downstream communication with a depentanizer overhead line 182. The depentanizer column may be operated with a top pressure of about 69 to about 517 kPa (gauge) (10 to 75 psig) and a bottom temperature of about 121 to about 232° C. (250 to 450° F.).

In the separation unit 200, $C_5$ materials comprising olefins and paraffins are separated with $C_5$ olefins recovered from the separation unit in the line 202 and $C_5$ paraffins recovered in the line 206. The separation unit 200 may be in downstream communication with the overhead line 164 and the bottoms line 166 of the debutanizer column 160 and the overhead line 182 of the depentanizer column 180. The $C_5$ paraffin stream in line 206 can be forwarded to the gasoline product pool or be further processed.

In an embodiment, the debutanizer column 160 can be operated as a depentanizer column to recover $C_5-$ materials in the overhead stream and $C_6$+ materials in the bottoms stream. In such an embodiment, the LPG splitter column can operate to send a $C_4$ and $C_5$ stream in the bottoms line 176 to the separation unit 200 for recovery of $C_4$ and $C_5$ olefins together. This embodiment is not shown.

In an embodiment, $C_4$ and $C_5$ olefinic material in a separated stream in line 202 may be delivered as a second hydrocarbon feed to a second catalytic reactor 300 which is in downstream communication with an overhead of the main fractionation column 100, a bottom of the primary absorber column 140, an overhead of the debutanizer column 160, a bottom of the LPG splitter column 170, an overhead of the depentanizer column 180 and the separation unit 200. The second catalytic reactor 300 may be a fluidized bed reactor, a fixed bed reactor or an ebullating bed reactor. The second catalytic reactor 300 may be a second FCC reactor. Although the second reactor 300 is depicted as a second FCC reactor, it should be understood that any suitable catalytic reactor can be utilized. The second catalytic reactor may also be an olefin cracking reactor or an oligomerization reactor. For purposes of the description of FIG. 1, the second catalytic reactor will be treated as a second FCC reactor.

The second hydrocarbon feed stream may be fed to the second FCC reactor 300 in line 202. The second hydrocarbon feed stream is preferably a portion of the first cracked products produced in the first catalytic reactor 10, fractionated in the fractionation section 90 and provided to the second reactor 300. In an embodiment, the second reactor is in downstream communication with the fractionation section 90, the separation unit 200 and/or the first reactor 10 which is in upstream communication with the product fractionation section 90.

The second hydrocarbon feed is contacted with catalyst in the second catalytic reactor 300 to produce upgraded products in a second effluent stream. The catalyst may be fluidized by inert gas. Generally, the second reactor 300 may operate under conditions to convert the light olefinic naphtha feed to smaller hydrocarbon products. $C_4$ olefins and $C_5$ olefins and paraffins crack into one or more light olefins, such as ethylene and/or propylene. A second effluent from the second catalytic reactor comprising a mixture of gaseous, upgraded product hydrocarbons in the line 301 may be combined with the first effluent of the first catalytic reactor in the line 87 for delivery to the fractionation section 90 via the line 88. Alternatively, another unshown line may deliver the second effluent to the fractionation section 90 separately from the first effluent in line 87. The fractionation section 90 may separately fractionate the second effluent stream into several streams which all may be generally referred to as a second effluent stream.

In some embodiments, the second catalytic reactor 300 can contain a mixture of the first and second catalyst components as described above for the first reactor. In one preferred embodiment, the second reactor 300 can contain less than about 20 wt %, preferably less than about 5 wt % of the first component and at least 20 wt % of the second component. In another preferred embodiment, the second reactor 300 can contain only the second component, preferably a MFI zeolite, as the catalyst. Coked catalyst from the second reactor 300 may also be regenerated in the regenerator 30 or otherwise heated without or with minimal regeneration and recycled back to the second reactor 300.

The second reactor 300 can operate in any suitable condition, such as a temperature of about 425° to about 705° C., preferably a temperature of about 550° to about 650° C., and a pressure of about 40 to about 700 kPa (gauge), preferably a pressure of about 40 to about 400 kPa (gauge), and optimally a pressure of about 50 to about 100 kPa (gauge). Typically, the residence time of the second reactor 300 can be less than about 5 seconds and preferably is between about 0.3 and about 1 seconds. Exemplary risers and operating conditions are disclosed in, e.g., U.S. Pat. No. 7,247,233 and U.S. Pat. No. 6,538,169.

It is contemplated that a portion of the $C_5$ paraffin stream in line 206 may be fed to the second catalytic reactor 300 but this embodiment is not shown in the FIGURES.

FIG. 2 shows the components of the separation unit 200 in detail. The first fractionation stream in LPG bottoms line 176 is passed to the separation unit 200 to produce a first separated stream in the line 202 having a greater concentration of $C_4$ olefins than the first fractionation stream in line 176. The separation unit 200 comprises a first distillation column 210 in downstream communication with the debutanizer column 160 particularly the LPG splitter column 170 for producing the first separated stream comprising $C_4$ olefins. In the embodiment of FIG. 2, the distillation column 210 may be an extractive distillation column. Paraffins and olefins enter the extractive distillation column 210 through the line 176 wherein the hydrocarbon materials in the first fractionation stream are contacted with a first extractant stream in line 212 which may be heat exchanged with the feed in line 176. The extraction distillation column 210 may be operated at a bottom temperature of 60° C. to 180° C., with a top temperature of 30° C. to 90° C., and an overhead pressure of about 275 to about 690 kPa (gauge) or otherwise appropriate to maintain the aforementioned temperature profile. The first extractant enters the extraction distillation column 210 at a higher elevation than the first fractionation stream in line 176. The ratio of solvent to hydrocarbon should be between about 2 and about 20 by weight.

In one embodiment, $C_4$ materials are contacted with the first extractant stream to selectively extract $C_4$ olefins from the first fractionation stream. An immiscible, biphasic mixture is formed, wherein the $C_4$ olefins selectively partition into an extract phase along with the extractant while the $C_4$ paraffins remain in a raffinate phase. The $C_4$ materials may further comprise additional trace hydrocarbons which may also partition into the extract phase. In the first extractive distillation column 210, the residual $C_4$ paraffins in the first fractionation stream separate from a first extraction stream of extractant and $C_4$ olefins. The raffinate phase composed predominantly of the $C_4$ paraffins is recovered from the extraction vessel 210 in a first raffinate overhead stream through an overhead line 214 and condensed. A portion of the first raffinate stream in line 214 can be returned to the first extractive distillation column 210 through a line 216 with the remainder of the first raffinate stream sent on for further processing through a line 203.

In certain embodiments the first extractant is a chemical compound selected from the group consisting of aminonitrobenzene, such as 4-aminonitrobenzene, nitromethane, dinitrobenzene, such as 1,4-dinitrobenzene, sulfolane, aniline, methylformamide, methyl imidazol, pyrimidine, pyrrol, acetamide and pyridazine. The preferred extractant is acetonitrile and dimethylformamide.

A first extraction stream composed predominantly of the $C_4$ olefins and the first extractant is recovered from the first extractive distillation column 210 through a bottoms line 218. A distillation recovery column 220 is in downstream communication with the bottoms line 218 of the first distillation column 210. A portion 217 of the first extraction stream may be reboiled and returned to the first extractive distillation column 210. The remaining first extraction stream in line 218 may be heated and passed to the distillation recovery column 220.

The distillation recovery column 220 is operated in a manner so as to effect a separation of the extractant from the extract, $C_4$ olefins, and additionally other trace hydrocarbons. Preferably, the separation is based on a difference in boiling points between the extractant and the $C_4$ olefins. The distillation recovery column 220 may contain trays, plates or an alternative packing material to effect the separation. The distillation recovery column 220 may be operated with a bottoms temperature between about 100 and about 220° C. and preferably between about 140 and about 200° C. and a pressure between about 70 and about 700 kPa (gauge). In one example, a bottoms stream containing the higher boiling extractant is recovered from the distillation recovery column 220 through a bottoms line 222 which is in downstream communication with the first extractive distillation column 210. A portion of the extractant in the bottoms line 222 may be reboiled and returned to the recovery column 220.

A separated stream composed of the $C_4$ olefins and optionally other trace hydrocarbons is recovered from the first extraction stream in the distillation recovery column 220 through an overhead line 224 and condensed. A portion of the separated stream which may be an extract stream in overhead line 224 can be returned to the distillation recovery column 220 through a line 226 with the remainder of the extract phase sent on for further processing as described in FIG. 1 by way of the line 202. Specifically, the net overhead line 202 on the recovery column 220 carries an extract comprising $C_4$ olefins to the second catalytic reactor which is in downstream communication with the recovery net overhead line 202 and the first extractive distillation column 210.

A first recycle portion of the net bottoms stream 228 may be recycled as the first extractant stream in line 212 to the first extractive distillation column, which is therefore in downstream communication with a bottoms line 222 of the recovery column 220.

It is contemplated that if the debutanizer column 160 is run as a depentanizer column to allow $C_5$ hydrocarbons into the overhead stream in overhead line 164 in an alternative embodiment of FIG. 1, such that the LPG splitter column sends $C_4$ and $C_5$ hydrocarbons to the separation unit 200 in line 176, $C_5$ olefins and $C_5$ paraffins may be produced in the separated stream in overhead line 202. However, in a preferred operation, a depentanizer column is utilized in addition to the debutanizer column in the preferred embodiment of FIG. 1 and the separation unit 200 may include a second extractive distillation column 230.

The second fractionation stream in the depentanizer overhead line 182 is passed to the separation unit 200 to produce a second separated stream in a second separated line 202 having a greater concentration of $C_5$ olefins than in the second fractionation stream in the depentanizer overhead line 182. In the preferred embodiment, the separation unit 200 comprises a second distillation column 230 in downstream communication with the debutanizer column 160 particularly the depentanizer column 180 for producing the second separated stream comprising $C_5$ olefins.

In the embodiment of FIG. 2, the second distillation column 230 may be a second extractive distillation column. Paraffins and olefins enter the second extractive distillation column 230 through the line 182 wherein the hydrocarbon materials in the second fractionation stream are contacted with a second extractant stream in line 232 which may be heat exchanged with the feed in line 182. The second extractive distillation column 230 may be operated at a bottom temperature of 60° C. to 180° C., with a top temperature of 30° C. to 90° C., and an overhead pressure of about 275 to about 690 kPa (gauge) or otherwise appropriate to maintain the aforementioned temperature profile. The second extractant in line 232 enters the extraction vessel 230 at a higher elevation than the second fractionation stream in line 182. The ratio of solvent to hydrocarbon should be between about 2 and about 20 by weight.

In one embodiment, $C_5$ materials are contacted with the second extractant stream to selectively extract $C_5$ olefins from the second fractionation stream. An immiscible, biphasic mixture is formed, wherein the $C_5$ olefins selectively partition into an extract phase along with the extractant while the $C_5$ paraffins remain in a raffinate phase. The $C_5$ materials may further comprise additional trace hydrocarbons which may also partition into the extract phase. In the second extractive distillation column 230, the residual $C_5$ paraffins in the first fractionation stream separate from a second extraction stream of extractant and $C_5$ olefins. The raffinate phase composed predominantly of the $C_5$ paraffins is recovered from the second distillation column 230 in a second raffinate overhead stream through an overhead line 234 and condensed. A portion of the $C_5$ second raffinate stream in line 234 can be returned to the second extractive distillation column 230 through a line 236 with the remainder of the first raffinate stream sent on for further processing through a line 206.

In certain embodiments the second extractant is a chemical compound selected from the group consisting of aminonitrobenzene, such as 4-aminonitrobenzene, nitromethane, dinitrobenzene, such as 1,4-dinitrobenzene, sulfolane, aniline, methylformamide, methyl imidazol, pyrimidine, pyrrol, acetamide and pyridazine. The preferred extractant is acetonitrile and dimethylformamide. In a preferred embodiment, the second extractant and the first extractant are the same.

A second extraction stream composed predominantly of the $C_5$ olefins and the second extractant is recovered from the second extractive distillation column 230 through a bottoms line 238. A distillation recovery column 220 is in downstream communication with the bottoms line 238 of the second extractive distillation column 230. A portion 237 of the second extraction stream may be reboiled and returned to the second extractive distillation column 230. The remaining second extraction stream in line 238 may be heated and passed to the distillation recovery column 220.

The distillation recovery column 220 is operated in a manner so as to effect a separation of the extractant from the extract, $C_5$ olefins, and additionally other trace hydrocarbons. Preferably, the separation is based on a difference in boiling points between the extractant and the $C_5$ olefins. The distillation recovery column 220 may contain trays, plates or an alternative packing material to effect the separation. The distillation recovery column 220 may be operated with a bottoms temperature between about 80 and about 200° C. and preferably between about 120 and about 180° C. and a pressure between about 70 and about 700 kPa (gauge). In one example, a bottoms stream containing the higher boiling extractant is recovered from the distillation recovery column 220 through a bottoms line 222 which is in downstream communication with the second extractive distillation column 230. A portion of the extractant in the bottoms line 222 may be reboiled and returned to the recovery column.

A separated stream composed of the $C_5$ olefins and optionally other trace hydrocarbons is recovered from the second extraction stream in the distillation recovery column 220 through a line 224 and condensed. A portion of the separated stream which may be an extract stream in overhead line 224 can be returned to the distillation recovery column 220 through a line 226 with the remainder of the extract phase sent on as the second separated stream for further processing as described in FIG. 1 by way of the line 202. Specifically, the net overhead line 202 on the recovery column 220 carries an extract comprising $C_5$ olefins to the second catalytic reactor which is in downstream communication with the recovery overhead line 202 and the second extractive distillation column 230.

A second recycle portion of the recovery net bottoms stream in line 228 may be recycled as the second extractant stream in line 232 to the second extractive distillation column, which is therefore in downstream communication with a bottoms line of the recovery column 220. In an embodiment, the distillation recovery column 220 is shared between the first extractive distillation column 210 and the second extractive distillation column 230. Sharing the same extractant enables sharing of the recovery column 220. Accordingly, the recovery column 220 may produce a combined first separated stream of $C_4$ olefins and second separated stream of $C_5$ olefins which may be a first extract stream and a second extract stream, respectively, in the recovery overhead line 202 and transported to the second catalytic reactor as described with respect to FIG. 1. A combined recycle portion of the recovery net bottoms stream in line 228 may be split and recycled as the first extractant stream in line 212 to the first extractive distillation column 210 and the second extractant stream in line 232 to the second extractive distillation column, which is therefore in downstream communication with the bottoms line 222 of the recovery column 220.

One unique feature of the disclosed apparatus and process is that the configuration allows for the advantages of a traditional FCC unit configuration, but improves the overall configuration by allowing for the $C_4$ and $C_5$ paraffins to be separated from the $C_4$ and $C_5$ olefins. We have surprisingly found that combining a first reactor with a fractionation section, a separation unit for processing the $C_4$ and $C_5$ materials and a second reactor not only results in a higher ethylene and propylene yield, but also reduces the capital cost and utility cost when compared to process with a second product recovery section. In regard to the present invention, the overall process recovery section is simplified compared to a process with a separation unit as a common fractionation section can be used. This approach results in less dilution of the hydrocarbon feed to the second reactor with paraffins hence providing a feed richer in olefins. With less dilution of the hydrocarbon feed with paraffins, the hydrocarbon feed rate is lower to the second catalytic reactor 300. The disclosed apparatus and process can provide ethylene and propylene yields greater than 20% (e.g., about 25%).

Turning now to FIG. 3, another embodiment of the present invention is an apparatus and process that may be described with reference to four components shown in FIG. 3: a first catalytic reactor 10, a fractionation section 90, a separation unit 200, and an olefin cracking reactor 300'. The embodiment of FIG. 3 differs from the embodiment of FIG. 1 in that the second catalytic reactor 300 of FIG. 1 has been removed and replaced with the olefin cracking reactor 300' and a second effluent line 301'. The olefin cracking reactor 300' is in fluid communication with the LPG splitter column 170 via line 301'. The similar components in FIG. 3 that were described above for FIGS. 1 and 2 will not be described again for FIG. 3.

In the apparatus of FIG. 3, the combined first and second separated stream containing $C_4$ and $C_5$ olefins from line 202 is introduced into the olefin cracking reactor 300', such as in the form of a fixed bed reactor, and the combined first and second separated stream contacts with an olefin cracking catalyst at reaction conditions effective to convert $C_4$ and $C_5$ olefins to form a second effluent stream in line 301'. The second effluent stream comprises $C_2$ and $C_3$ olefins. Catalysts suitable for olefin cracking comprise a crystalline silicate of the MFI family which may be a zeolite, a silicalite or any other silicate in that family or the MEL family which may be a zeolite or any other silicate in that family. Examples of MFI silicates are ZSM-5 and Silicalite. An example of an MEL zeolite is ZSM-11. Other examples are Boralite D and Silicalite-2 as described by the International Zeolite Association, Atlas of Zeolite Structure Types. The preferred crystalline silicates have pores or channels defined by ten oxygen rings and a high silicon/aluminum atomic ratio typically of at least 120, and preferably over 1500, attained by suitable dealumination methods.

The catalyst has structural and chemical properties and is employed under particular reaction conditions whereby the catalytic cracking of the $C_4$ and $C_5$ olefins readily proceeds. Different reaction pathways can occur on the catalyst. Suitable olefin cracking process conditions include a temperature of around 400 to 600° C., preferably from 500 to 600° C., and a pressure of from 100 to 500 kPa.

As shown in FIG. 3, the cracked olefins effluent stream from the olefin cracking reactor 300' can be appropriately processed by being returned to the LPG splitter column 170 via line 301'. The cracked olefins effluent stream may include ethylene and propylene. In the LPG splitter column 170, $C_2$ and $C_3$ materials may be forwarded from the overhead in a line 174 to an ethylene recovery unit to recover ethylene product and a propylene recovery unit to recover propylene product. The bottom stream in line 176 may be sent to the separation unit 200 for further processing as described above.

EXAMPLES

Example 1

A model feed of expected FCC composition for the first fractionation stream and the second fractionation stream subjected to the separation in a simulation separation unit under the conditions in Table 1 would be expected to produce the yields in Tables 2 and 3. The extractant used was acetonitrile. The "olefin" row in Tables 2 and 3 represents the fraction of olefins in the extract stream. The "recovery" row represents the ratio of olefins fraction in the extract stream to the olefins fraction in the feed stream.

TABLE 1

| Column | $C_4$ Extractive Distillation 210 | Recovery Column 220 | $C_5$ Extractive Distillation 230 |
|---|---|---|---|
| Overhead | | | |
| Temperature, ° C. | 49 | 49 | 49 |
| Pressure, kPa (gauge) | 380 | 290 | 97 |
| Bottom | | | |
| Temperature, ° C. | 115 | 138 | 76 |
| Pressure, kPa (gauge) | 448 | 359 | 165 |

TABLE 2

Typical Yields
Separate Butanes from Butenes

| Components, wt % | $C_4$ Feed | Product Raffinate | Extract |
|---|---|---|---|
| i-Butane | 22.3 | 75.0 | 1.5 |
| n-Butane | 6.6 | 20.5 | 1.1 |
| Isobutylene | 26.2 | 1.7 | 35.9 |
| n-Butenes | 44.7 | 2.7 | 61.2 |
| Butadiene | 0.2 | 0.0 | 0.3 |
| Total | 100.0 | 100.0 | 100.0 |
| Recovery, wt % | | | 98.2 |
| Olefin, wt % | 71.1 | 4.4 | 97.4 |

Butene recovery may exceed 98 wt %. We expect that butene recovery can be pushed as high as 99 wt %.

TABLE 3

Typical Yields
Separate Pentanes from Pentenes

| Component, wt % | $C_5$ Feed | Product Raffinate | Extract |
|---|---|---|---|
| i-Pentanes | 22.0 | 85.2 | 10.4 |
| n-Pentanes | 2.4 | 7.4 | 1.4 |
| Cyclo-Pentane | 1.3 | 2.6 | 1.1 |

TABLE 3-continued

Typical Yields
Separate Pentanes from Pentenes

| Component, wt % | $C_5$ Feed | Product Raffinate | Extract |
|---|---|---|---|
| i-Pentenes | 40.0 | 2.5 | 46.9 |
| n-Pentenes | 31.4 | 2.3 | 36.7 |
| Pentadiene | 3.0 | 0 | 3.5 |
| Total | 100.0 | 100.0 | 100.0 |
| Recovery, wt % | | | 99.0 |
| Olefin, wt % | 74.4 | 4.8 | 87.2 |

$C_5$ olefin recovery may exceed 99 wt %. $C_5$ olefin recovery may be increased if by allowing the extract stream to carry higher $C_5$ paraffin concentration. $C_5$ olefin concentration may be allowed to go to as low as about 60 wt % to about 80 wt % and suitably about 90 wt %.

Separate extractive distillation of $C_4$ and $C_5$ hydrocarbons will provide excellent separations. We expect to achieve separation with greater than or equal to about 90 wt %, suitably about 95 wt % and preferably about 99 wt % total olefin recovery for both the first fractionation stream and the second fractionation stream. The separation unit can be run to achieve higher separation for $C_4$ feed, because $C_4$ paraffin will build up as an inert in the recycle to the second reactor. However, we have found that high separation for $C_5$ feed may not be necessary, because $C_5$ paraffins will crack in the second catalytic reactor. Hence, higher olefin production can be achieved if some $C_5$ paraffins are recycled with $C_5$ olefins in the feed to the second reactor.

Example 2

A feed having the composition of Table 4 was mixed with acetonitrile solvent at a solvent to hydrocarbon ratio of 14:1 by weight at a range of 24 to 91° C. and a pressure of 97 to 629 kPa (gauge) (14 to 91 psig) and allowed to separate into vapor and liquid phases. The vapor phase has a higher paraffin concentration versus the liquid phase for both $C_4$ and $C_5$ mixture indicating a reasonable separation.

TABLE 4

Feed Composition

| Feed | wt % |
|---|---|
| Iso-Butane | 19.5% |
| 1-Butene and Isobutylene | 20.4% |
| Cis-2-butene | 17.8% |
| Trans-2-butene | 12.1% |
| Isopentane | 9.7% |
| 1-Pentene | 10.2% |
| 3-Methyl-1-Butene | 10.2% |

Figure 4:
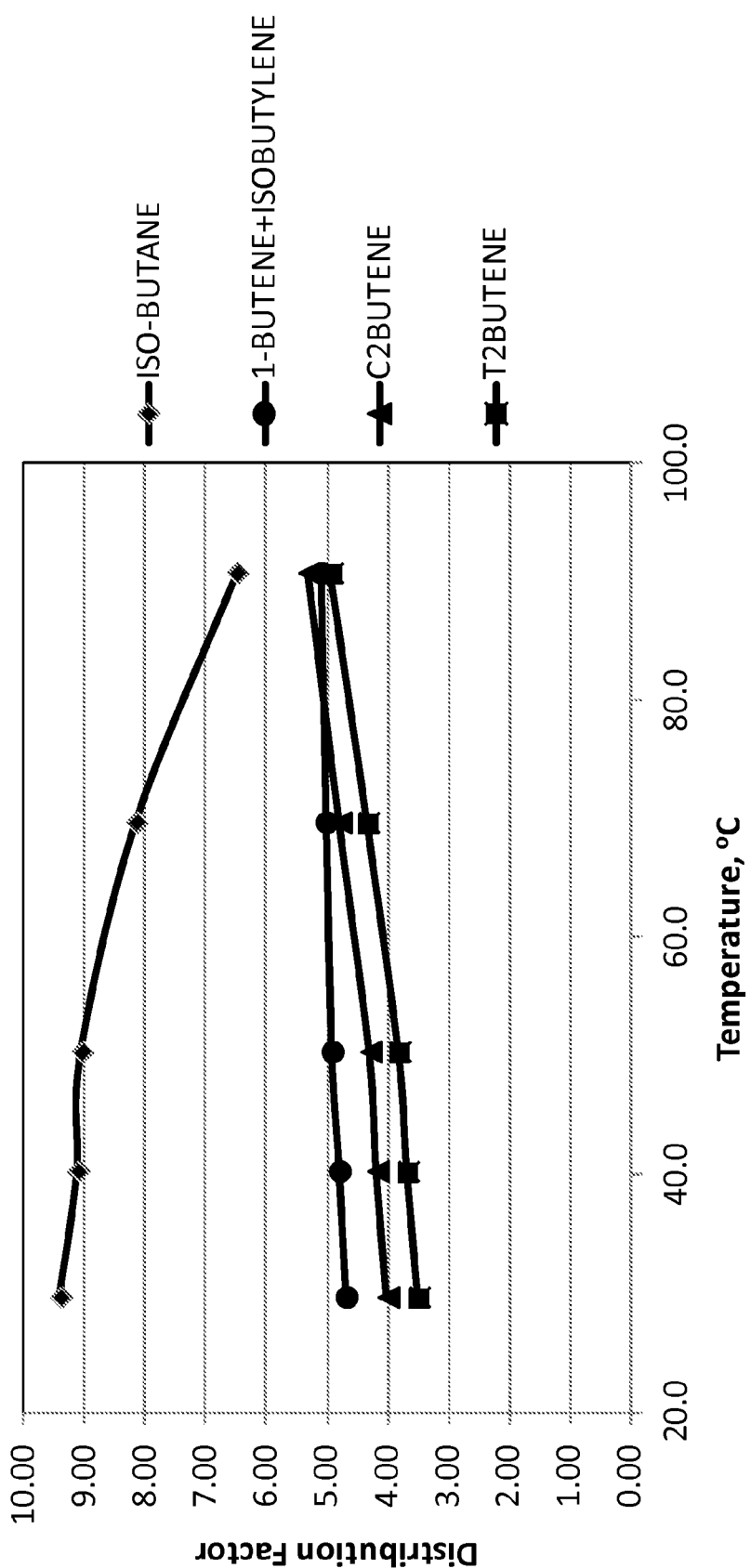
FIG. 4 is a plot of butene distribution factor versus temperature.

FIG. 4 shows the ratio of $C_4$ hydrocarbons in the vapor phase versus in the liquid phase, known as the Gas-Liquid Distribution Factor, by $C_4$ component at different temperatures. The Gas-Liquid Distribution Factor, K equals a mole ratio of the fraction of the component in the vapor phase to the fraction of the component in the liquid phase. FIG. 4 indicates that the separation is sensitive to temperature.

Figure 5:
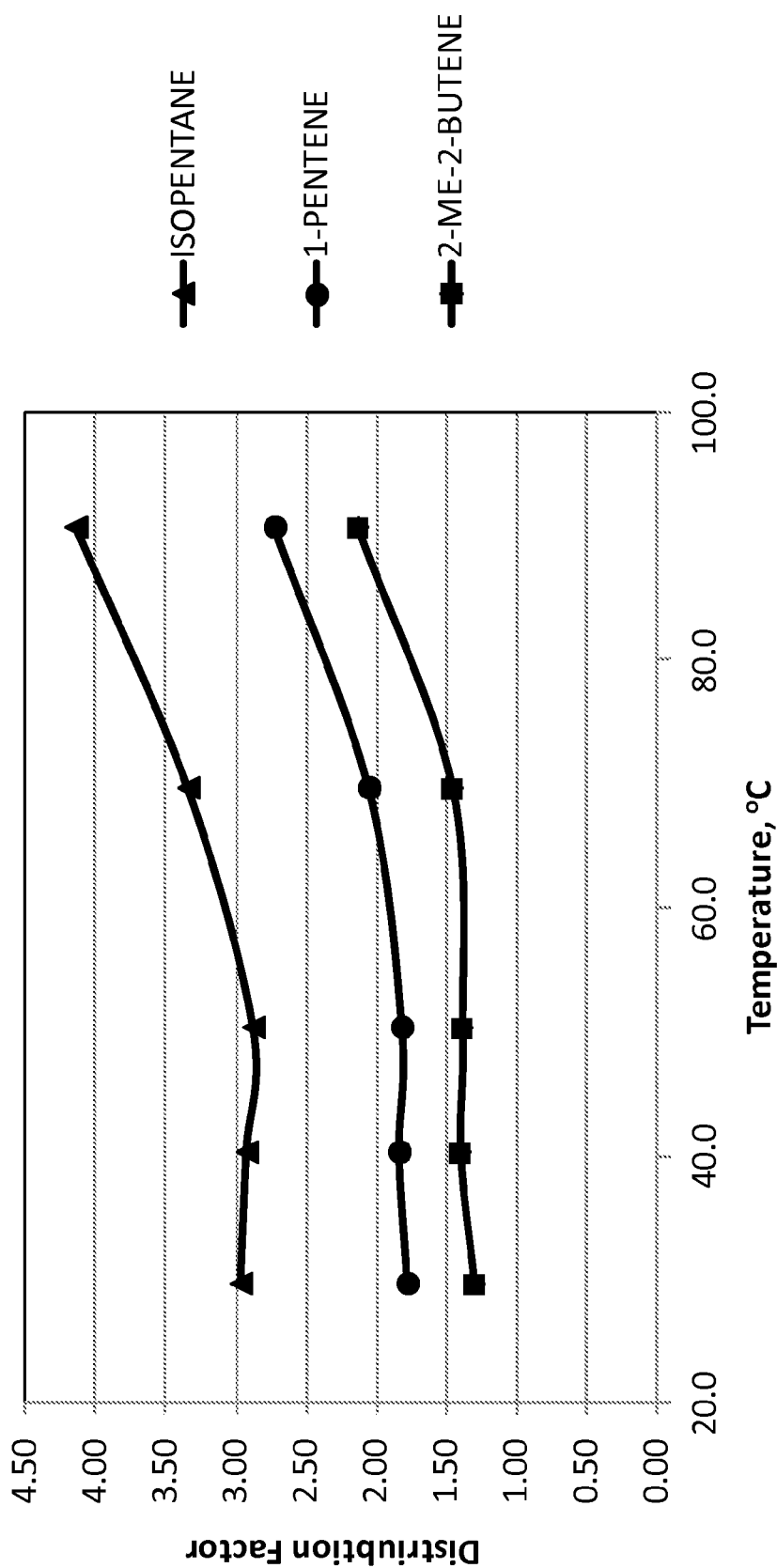
FIG. 5 is a plot of pentene distribution factor versus temperature.

FIG. 5 shows the ratio of $C_5$ hydrocarbons in the vapor phase versus in the liquid phase by $C_5$ component at different temperatures.

Although these separations are evaluated with $C_4$ and $C_5$ hydrocarbons together, separate extractions would provide better recoveries of olefins because less interaction of $C_4$ and $C_5$ components are expected. Additionally, using two distillation columns in the separation unit enables the first distillation column to be run to achieve greater separation of $C_4$ olefins while the second column can be run with lesser separation of $C_5$ olefins from paraffins. This arrangement allows higher olefin recovery, resulting in increased light olefin yield with less capital cost.

Specific Embodiments

While the following is described in conjunction with specific embodiments, it will be understood that this description is intended to illustrate and not limit the scope of the preceding description and the appended claims.

A first embodiment of the invention is a process for catalytic cracking, the process comprising (a) feeding a hydrocarbon feed stream to a first catalytic reactor; (b) passing an effluent stream of the first catalytic reactor to a fractionation section to produce a first fractionation stream, the first fractionation stream comprising $C_4$ hydrocarbons; (c) passing the first fractionation stream to a separation unit to produce a first separated stream having a greater concentration of $C_4$ olefins than the first fractionation stream; and (d) feeding the first separated stream to a second catalytic reactor. An embodiment of the invention is one, any or all of prior embodiments in this paragraph up through the first embodiment in this paragraph further comprising feeding a stream of $C_5$ olefins to the second catalytic reactor. An embodiment of the invention is one, any or all of prior embodiments in this paragraph up through the first embodiment in this paragraph wherein step (c) comprises (i) contacting the first fractionation stream with a first extractant stream to selectively extract $C_4$ olefins from the first fractionation stream; (ii) separating the residual $C_4$ paraffins in the first fractionation stream from a first extraction stream of extractant and $C_4$ olefins; and (iii) recovering the $C_4$ olefins from the first extraction stream to produce the first separated stream. An embodiment of the invention is one, any or all of prior embodiments in this paragraph up through the first embodiment in this paragraph wherein separating the residual $C_4$ paraffins from the first extraction stream is performed in a first extractive distillation column from which the $C_4$ paraffins are provided in a first raffinate overhead stream and the first extraction stream is provided in a bottoms stream. An embodiment of the invention is one, any or all of prior embodiments in this paragraph up through the first embodiment in this paragraph further comprising (e) producing a second fractionation stream comprising $C_5$ hydrocarbons from passing the effluent stream of the first catalytic reactor to the fractionation section; (f) passing the second fractionation stream to the separation unit to produce a second separated stream having a greater concentration of $C_5$ olefins than the second fractionation stream; and (g) feeding the second separated stream to the second catalytic reactor. An embodiment of the invention is one, any or all of prior embodiments in this paragraph up through the first embodiment in this paragraph wherein step (f) comprises (i) contacting the second fractionation stream with a second extractant stream to selectively extract $C_5$ olefins from the second fractionation section stream; (ii) separating the residual $C_5$ paraffins in the second fractionation section stream from a second extraction stream and $C_5$ olefins; and (iii) recovering the $C_5$ olefins from the second extraction stream to produce the second separated stream. An embodiment of the invention is one, any or all of prior embodiments in this paragraph up through the first embodiment in this paragraph wherein separating the residual $C_5$ paraffins from the second extraction stream is performed in a second extractive distillation column from which the $C_5$ paraffins are provided in a second raffinate overhead stream and the second extraction stream is provided in a bottoms stream. An embodiment of the invention is one, any or all of prior embodiments in this paragraph up through the first embodiment in this paragraph wherein steps (c) and (f) comprise (i) contacting the first fractionation stream with a first extractant stream to selectively extract $C_4$ olefins from the first fractionation stream; (ii) separating the residual $C_4$ paraffins in the first fractionation stream from a first extraction stream of extractant and $C_4$ olefins; and (iii) contacting the second fractionation stream with a second extractant stream to selectively extract $C_5$ olefins from the second fractionation stream; (iv) separating the residual $C_5$ paraffins in the second fractionation stream from a second extraction stream of extractant and $C_5$ olefins; and (v) recovering the $C_4$ olefins and the $C_5$ olefins from extractant to produce a combined first separated stream and second separated stream. An embodiment of the invention is one, any or all of prior embodiments in this paragraph up through the first embodiment in this paragraph wherein the step of recovering in step (v) is performed in the same recovery column in which the combined first separated stream and second separated stream are provided in an overhead stream and the first extractant stream and the second extractant stream are provided in a bottoms stream. An embodiment of the invention is one, any or all of prior embodiments in this paragraph up through the first embodiment in this paragraph wherein the step of passing an effluent stream of the first catalytic reactor to a fractionation section to produce a first fractionation stream comprises passing the effluent stream to a debutanizer column. An embodiment of the invention is one, any or all of prior embodiments in this paragraph up through the first embodiment in this paragraph further comprising passing an overhead stream from the debutanizer column to an LPG splitter column and the first fractionation stream is provided from a bottom of the LPG splitter. An embodiment of the invention is one, any or all of prior embodiments in this paragraph up through the first embodiment in this paragraph wherein the step of passing an effluent stream of the first catalytic reactor to a fractionation section to produce a second fractionation stream comprises passing the effluent stream to a depentanizer column and the second fractionation stream is provided from an overhead of the depentanizer column. An embodiment of the invention is one, any or all of prior embodiments in this paragraph up through the first embodiment in this paragraph wherein the extractants used in the extraction unit are selected from aminonitrobenzene, nitromethane, dinitrobenzene, sulfolane, aniline, methylformamide, methyl imidazol, pyrimidine, pyrrol, acetamide and pyridazine.

A second embodiment of the invention is a process for catalytic cracking, the process comprising (a) feeding a hydrocarbon feed stream to a first catalytic reactor; (b) passing an effluent stream of the first catalytic reactor to a fractionation section to produce a first fractionation stream, the first fractionation stream comprising $C_4$ hydrocarbons; (c) passing the first fractionation stream to an extraction unit to produce a first extract stream having a greater concentration of $C_4$ olefins than the first fractionation stream; (d) feeding the first extract stream to a second catalytic reactor; (e) producing a second fractionation stream comprising $C_5$ hydrocarbons from passing the effluent stream of the first catalytic reactor to the fractionation section; (f) passing the second fractionation stream to the extraction unit to produce a second extract stream having a greater concentration of $C_5$ olefins than the second fractionation stream; and (g) feeding the second extract stream to the second catalytic reactor. An embodiment of the invention is one, any or all of prior embodiments in this paragraph up through the second embodiment in this paragraph wherein steps (c) and (f) comprise (i) contacting the first fractionation stream with a first extractant stream to selectively extract $C_4$ olefins from the first fractionation stream; (ii) separating the residual $C_4$ paraffins in the first fractionation stream from a first extraction stream of extractant and $C_4$ olefins; (iii) contacting the second fractionation stream with a second extractant stream to selectively extract $C_5$ olefins from the second fractionation stream; (iv) separating the residual $C_5$ paraffins in the second fractionation stream from a second extraction stream of extractant and $C_5$ olefins; and (v) recovering the $C_4$ olefins and the $C_5$ olefins from extractant to produce a combined first extract stream and second extract stream. An embodiment of the invention is one, any or all of prior embodiments in this paragraph up through the second embodiment in this paragraph wherein separating the residual $C_4$ paraffins from the first extraction stream is performed in a first extractive distillation column from which the $C_4$ paraffins are provided in a first raffinate overhead stream and the first extraction stream is provided in a bottoms stream; separating the residual $C_5$ paraffins from the second extraction stream is performed in a second extractive distillation column from which the $C_5$ paraffins are provided in a second raffinate overhead stream and the second extraction stream is provided in a bottoms stream; and recovering in step (v) is performed in the same recovery column in which the combined first extract stream and second extract stream are provided in an overhead stream and the first extractant stream and the second extractant stream are provided in a bottoms stream. An embodiment of the invention is one, any or all of prior embodiments in this paragraph up through the second embodiment in this paragraph wherein the extractants used in the extraction unit are selected from aminonitrobenzene, nitromethane, dinitrobenzene, sulfolane, aniline, methylformamide, methyl imidazol, pyrimidine, pyrrol, acetamide and pyridazine.

A third embodiment of the invention is a process for catalytic cracking, the process comprising (a) feeding a hydrocarbon feed stream to a first catalytic reactor; (b) passing an effluent stream of the first catalytic reactor to a debutanizer column and a depentanizer column in a fractionation section to produce a first fractionation stream and a second fractionation stream comprising $C_5$ hydrocarbons; (c) passing the first fractionation stream to an extraction unit to produce a first extract stream having a greater concentration of $C_4$ olefins than the first fractionation stream; (d) passing the second fractionation stream to an extraction unit to produce a second extract stream having a greater concentration of $C_5$ olefins than the second fractionation stream; and (e) feeding the first extract stream and the second extract stream to a second catalytic reactor. An embodiment of the invention is one, any or all of prior embodiments in this paragraph up through the third embodiment in this paragraph further comprising passing an overhead stream from the debutanizer column to an LPG splitter column and the first fractionation stream is provided from a bottom of the LPG splitter column. An embodiment of the invention is one, any or all of prior embodiments in this paragraph up through the third embodiment in this paragraph wherein the step of passing a bottoms stream from the debutanizer column to the depentanizer column and the second fractionation stream is provided from an overhead of the depentanizer column.

A fourth embodiment of the invention is an apparatus for catalytic cracking, comprising a first catalytic reactor for catalytically cracking a first hydrocarbon feed stream; a fractionation zone in downstream communication with the first catalytic reactor, the fractionation zone comprising a debutanizer column; a separation unit including a first distillation column in downstream communication with the debutanizer column for producing a first separated stream comprising $C_4$ olefins; and a second catalytic reactor in downstream communication with the separation unit for cracking a second hydrocarbon feed stream comprising the first separated stream. An embodiment of the invention is one, any or all of prior embodiments in this paragraph up through the fourth embodiment in this paragraph wherein the separation unit comprises a second distillation column in downstream communication with the fractionation section for producing a second separated stream comprising $C_5$ olefins. An embodiment of the invention is one, any or all of prior embodiments in this paragraph up through the fourth embodiment in this paragraph further comprising a recovery column in the separation unit for separating extractant from extract, the recovery column being in downstream communication with the first distillation column and the second distillation column. An embodiment of the invention is one, any or all of prior embodiments in this paragraph up through the fourth embodiment in this paragraph wherein the first distillation column and the second distillation column are in downstream communication with a bottoms line of the recovery column. An embodiment of the invention is one, any or all of prior embodiments in this paragraph up through the fourth embodiment in this paragraph further comprising an overhead line on the recovery column for carrying an extract comprising $C_4$ olefins and $C_5$ olefins, the second catalytic reactor being in downstream communication with the overhead line. An embodiment of the invention is one, any or all of prior embodiments in this paragraph up through the fourth embodiment in this paragraph wherein the recovery column is in downstream communication with a bottoms line of the first distillation column and the second distillation column. An embodiment of the invention is one, any or all of prior embodiments in this paragraph up through the fourth embodiment in this paragraph wherein the second catalytic reactor is in downstream communication with the first distillation column and the second distillation column. An embodiment of the invention is one, any or all of prior embodiments in this paragraph up through the fourth embodiment in this paragraph wherein the separation unit is in downstream communication with an overhead line and a bottoms line of the debutanizer column. An embodiment of the invention is one, any or all of prior embodiments in this paragraph up through the fourth embodiment in this paragraph further comprising a LPG splitter column in downstream communication with the debutanizer column, and the separation unit is in downstream communication with the LPG splitter. An embodiment of the invention is one, any or all of prior embodiments in this paragraph up through the fourth embodiment in this paragraph further comprising a depentanizer column in downstream communication with the debutanizer column and the separation unit is in downstream communication with an overhead line of the depentanizer column. An embodiment of the invention is one, any or all of prior embodiments in this paragraph up through the fourth embodiment in this paragraph wherein the first distillation column is in downstream communication with the debutanizer column and the second distillation column is in downstream communication with the depentanizer column.

A fifth embodiment of the invention is an apparatus for catalytic cracking, comprising a first catalytic reactor for catalytically cracking a first hydrocarbon feed stream; a fractionation zone in downstream communication with the first catalytic reactor, the fractionation zone comprising a debutanizer column; an extraction unit including a first extractive distillation column in downstream communication with the debutanizer column for producing a first extract stream comprising $C_4$ olefins and a second extractive distillation column for producing a second extract stream comprising $C_5$ olefins; and a second catalytic reactor in downstream communication with the extraction unit for cracking a second hydrocarbon feed stream. An embodiment of the invention is one, any or all of prior embodiments in this paragraph up through the fifth embodiment in this paragraph wherein the second extractive distillation column is in downstream communication with the debutanizer column. An embodiment of the invention is one, any or all of prior embodiments in this paragraph up through the fifth embodiment in this paragraph wherein the fractionation zone further comprises a depentanizer column and the second extractive distillation column is in downstream communication with the depentanizer column. An embodiment of the invention is one, any or all of prior embodiments in this paragraph up through the fifth embodiment in this paragraph wherein the depentanizer column is in downstream communication with the debutanizer column.

A sixth embodiment of the invention is an apparatus for catalytic cracking, comprising a first catalytic reactor for catalytically cracking a first hydrocarbon feed stream; a fractionation zone in downstream communication with the first catalytic reactor, the fractionation zone comprising a debutanizer column; an extraction unit including a first extractive distillation column in downstream communication with the debutanizer column for producing a first extract stream comprising $C_4$ olefins and a second extractive distillation column in downstream communication with the fractionation zone for producing a second extract stream comprising $C_5$ olefins; and a second catalytic reactor in downstream communication with the extraction unit for cracking a second hydrocarbon feed stream comprising the first extract stream. An embodiment of the invention is one, any or all of prior embodiments in this paragraph up through the sixth embodiment in this paragraph wherein the extraction unit further comprises a recovery column for separating extractant from extract, the recovery column being in downstream communication with the first extractive distillation column and the second extractive distillation column and producing a combined stream of the first extract and the second extract and the second catalytic reactor in downstream communication with the recovery column. An embodiment of the invention is one, any or all of prior embodiments in this paragraph up through the sixth embodiment in this paragraph wherein the first extractive distillation column and the second extractive distillation column are in downstream communication with a bottoms line of the recovery column. An embodiment of the invention is one, any or all of prior embodiments in this paragraph up through the sixth embodiment in this paragraph further comprising a LPG splitter column in downstream communication with the debutanizer column, and the extraction unit is in downstream communication with the LPG splitter column. An embodiment of the invention is one, any or all of prior embodiments in this paragraph up through the sixth embodiment in this paragraph further comprising a depentanizer column in downstream communication with the debutanizer column and the extraction unit is in downstream communication with an overhead line of the depentanizer column.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. An apparatus for catalytic cracking, comprising:
   a first catalytic reactor for catalytically cracking a first hydrocarbon feed stream;
   a fractionation zone in downstream communication with the first catalytic reactor, said fractionation zone comprising a debutanizer column;
   a separation unit including a first distillation column in downstream communication with said debutanizer column for producing a first separated stream comprising $C_4$ olefins and a second distillation column in downstream communication with said fractionation section for producing a second separated stream comprising $C_5$ olefins and a recovery column in said separation unit for separating extractant from extract, said recovery column being in downstream communication with said first distillation column and said second distillation column; and
   a second catalytic reactor in downstream communication with an overhead line of said first distillation column and an overhead line of said second distillation column of the separation unit for cracking a second hydrocarbon feed stream comprising said first separated stream and said second separated stream.

2. The apparatus of claim 1 wherein said first distillation column and said second distillation column are in downstream communication with a bottoms line of said recovery column.

3. The apparatus of claim 2 further comprising an overhead line on said recovery column for carrying an extract comprising $C_4$ olefins and $C_5$ olefins, said second catalytic reactor being in downstream communication with said overhead line.

4. The apparatus of claim 1 wherein said recovery column is in downstream communication with a bottoms line of said first distillation column and said second distillation column.

5. The apparatus of claim 1 wherein said separation unit is in downstream communication with an overhead line and a bottoms line of said debutanizer column.

6. The apparatus of claim 1 further comprising a LPG splitter column in downstream communication with said debutanizer column, and said separation unit is in downstream communication with said LPG splitter.

7. The apparatus of claim 1 further comprising a depentanizer column in downstream communication with said debutanizer column and said separation unit is in downstream communication with an overhead line of said depentanizer column.

8. The apparatus of claim 7 wherein said first distillation column is in downstream communication with said debutanizer column and said second distillation column is in downstream communication with said depentanizer column.

9. An apparatus for catalytic cracking, comprising:
   a first catalytic reactor for catalytically cracking a first hydrocarbon feed stream;
   a fractionation zone in downstream communication with the first catalytic reactor, said fractionation zone comprising a debutanizer column;
   an extraction unit including a first extractive distillation column in downstream communication with said debutanizer column for producing a first extract stream comprising $C_4$ olefins, a second extractive distillation column for producing a second extract stream comprising $C_5$ olefins and a recovery column in connection with a bottoms line of said first distillation column and a bottoms line of said second distillation column; and
   a second catalytic reactor in downstream communication with the extraction unit for cracking a second hydrocarbon feed stream.

10. The apparatus of claim 9 wherein said second extractive distillation column is in downstream communication with said debutanizer column.

11. The apparatus of claim 9 wherein said fractionation zone further comprises a depentanizer column and said second extractive distillation column is in downstream communication with said depentanizer column.

12. The apparatus of claim 11 wherein said depentanizer column is in downstream communication with said debutanizer column.

13. An apparatus for catalytic cracking, comprising:
   a first catalytic reactor for catalytically cracking a first hydrocarbon feed stream;
   a fractionation zone in downstream communication with the first catalytic reactor, said fractionation zone comprising a debutanizer column, a LPG splitter column in downstream communication with said debutanizer column and a depentanizer column in downstream communication with said debutanizer column;
   an extraction unit including a first extractive distillation column in downstream communication with said debutanizer column for producing a first extract stream comprising $C_4$ olefins and a second extractive distillation column in downstream communication with said fractionation zone for producing a second extract stream comprising $C_5$ olefins, said extraction unit in downstream communication with said LPG splitter column and said depentanizer column; and
   a second catalytic reactor in downstream communication with an overhead line of said first extractive distillation column and an overhead line of said second extractive distillation column of the extraction unit for cracking a second hydrocarbon feed stream comprising said first extract stream and said second extract stream.

14. The apparatus of claim 13 wherein said extraction unit further comprises a recovery column for separating extractant from extract, said recovery column being in downstream communication with said first extractive distillation column and said second extractive distillation column and producing a combined stream of said first extract and said second extract and said second catalytic reactor in downstream communication with said recovery column.

15. The apparatus of claim 14 wherein said first extractive distillation column and said second extractive distillation column are in downstream communication with a bottoms line of said recovery column.

* * * * *